United States Patent
Maschino et al.

(10) Patent No.: US 11,083,641 B2
(45) Date of Patent: Aug. 10, 2021

(54) METHOD OF MANUFACTURING AN ACTIVATED COMPOSITE WEB AND AN ACTIVATED COMPOSITE WEB FOR ABSORPTIVE DEVICES

(71) Applicant: FITESA FILM PRODUCTS LLC, Simpsonville, SC (US)

(72) Inventors: Andrew D. Maschino, Paris, IL (US); Brian C. Loomis, Terre Haute, IN (US); Todd R. Skochdopole, Moseley, VA (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 0 days.

(21) Appl. No.: 16/845,206

(22) Filed: Apr. 10, 2020

(65) Prior Publication Data
US 2020/0237579 A1   Jul. 30, 2020

Related U.S. Application Data

(63) Continuation of application No. 15/918,803, filed on Mar. 12, 2018, now Pat. No. 10,617,575.
(Continued)

(51) Int. Cl.
*B32B 3/24* (2006.01)
*B32B 27/12* (2006.01)
(Continued)

(52) U.S. Cl.
CPC .... *A61F 13/5126* (2013.01); *A61F 13/15699* (2013.01); *A61F 13/513* (2013.01);
(Continued)

(58) Field of Classification Search
None
See application file for complete search history.

(56) References Cited

U.S. PATENT DOCUMENTS

| 3,929,135 A | 12/1975 | Thompson |
| 4,252,516 A | 2/1981 | Raley et al. |

(Continued)

FOREIGN PATENT DOCUMENTS

| CN | 1764533 A | 4/2006 |
| CN | 101395315 B | 3/2009 |

(Continued)

OTHER PUBLICATIONS

Machine Translation of JP-2004098356-A, Apr. 2004 (Year: 2004).*
(Continued)

*Primary Examiner* — Jeffrey A Vonch
(74) *Attorney, Agent, or Firm* — Karceski IP Law, PLLC

(57) ABSTRACT

A method of manufacturing an activated composite web includes laminating a film layer to a nonwoven web to form a composite web, forming a plurality of apertured protuberances in the film layer, and passing the composite web through intermeshing elements to form an activated composite web. The intermeshing elements form a plurality of first lanes, with first widths, substantially unaffected by activation, and a plurality of second lanes, with second widths. The second widths are less than the first widths. Portions of the plurality of apertured protuberances define first apertures in the first lanes and second apertures in the second lanes. The cross-sections of the second apertures are larger than the first apertures. The first apertures have their major axes substantially aligned in the first direction while the second apertures have their major axis substantially aligned in the second direction. An activated composite web also is provided.

8 Claims, 9 Drawing Sheets

Related U.S. Application Data

(60) Provisional application No. 62/470,671, filed on Mar. 13, 2017.

(51) Int. Cl.

| | | |
|---|---|---|
| *B32B 37/15* | (2006.01) | |
| *B32B 38/04* | (2006.01) | |
| *B29C 55/08* | (2006.01) | |
| *B29C 55/18* | (2006.01) | |
| *A61F 13/512* | (2006.01) | |
| *B32B 3/26* | (2006.01) | |
| *B32B 3/30* | (2006.01) | |
| *B32B 37/00* | (2006.01) | |
| *B29C 41/26* | (2006.01) | |
| *B29C 41/30* | (2006.01) | |
| *B29C 41/50* | (2006.01) | |
| *A61F 13/511* | (2006.01) | |
| *A61F 13/15* | (2006.01) | |
| *B32B 5/02* | (2006.01) | |
| *B32B 5/14* | (2006.01) | |
| *B29C 55/02* | (2006.01) | |
| *B29C 55/06* | (2006.01) | |
| *A61F 13/513* | (2006.01) | |
| *A61F 13/537* | (2006.01) | |
| *B32B 5/04* | (2006.01) | |
| *B32B 7/04* | (2019.01) | |
| *B32B 27/32* | (2006.01) | |
| *B32B 38/00* | (2006.01) | |
| *B32B 3/28* | (2006.01) | |
| *B29C 55/00* | (2006.01) | |

(52) U.S. Cl.
CPC .... *A61F 13/5121* (2013.01); *A61F 13/51108* (2013.01); *A61F 13/537* (2013.01); *A61F 13/5376* (2013.01); *B29C 41/26* (2013.01); *B29C 41/30* (2013.01); *B29C 41/50* (2013.01); *B29C 55/023* (2013.01); *B29C 55/06* (2013.01); *B29C 55/18* (2013.01); *B32B 3/266* (2013.01); *B32B 3/30* (2013.01); *B32B 5/022* (2013.01); *B32B 5/142* (2013.01); *B32B 5/147* (2013.01); *B32B 27/12* (2013.01); *B32B 37/0053* (2013.01); *B32B 37/15* (2013.01); *A61F 13/15203* (2013.01); *A61F 13/53747* (2013.01); *A61F 2013/15406* (2013.01); *A61F 2013/15715* (2013.01); *A61F 2013/5127* (2013.01); *A61F 2013/53765* (2013.01); *A61F 2013/53782* (2013.01); *A61F 2013/53786* (2013.01); *B29C 55/005* (2013.01); *B29C 55/026* (2013.01); *B32B 3/28* (2013.01); *B32B 5/04* (2013.01); *B32B 7/04* (2013.01); *B32B 27/32* (2013.01); *B32B 2038/0028* (2013.01); *B32B 2038/047* (2013.01); *B32B 2250/02* (2013.01); *B32B 2250/24* (2013.01); *B32B 2250/242* (2013.01); *B32B 2307/718* (2013.01); *B32B 2307/726* (2013.01); *B32B 2555/02* (2013.01); *Y10T 156/1018* (2015.01); *Y10T 156/1056* (2015.01); *Y10T 156/1057* (2015.01); *Y10T 428/2457* (2015.01); *Y10T 428/24182* (2015.01); *Y10T 428/24273* (2015.01); *Y10T 428/24281* (2015.01); *Y10T 428/24322* (2015.01); *Y10T 428/24612* (2015.01); *Y10T 428/24694* (2015.01); *Y10T 428/24711* (2015.01); *Y10T 442/674* (2015.04); *Y10T 442/678* (2015.04); *Y10T 442/68* (2015.04); *Y10T 442/681* (2015.04)

(56) References Cited

U.S. PATENT DOCUMENTS

| | | |
|---|---|---|
| 4,323,069 A | 4/1982 | Ahr et al. |
| 4,324,246 A | 4/1982 | Mullane et al. |
| 4,324,247 A | 4/1982 | Aziz |
| 4,842,794 A | 6/1989 | Hovis et al. |
| 4,995,930 A | 2/1991 | Merz et al. |
| 5,028,289 A | 7/1991 | Rasmussen |
| 5,246,433 A | 9/1993 | Hasse et al. |
| 5,366,782 A | 11/1994 | Curro et al. |
| D362,120 S | 9/1995 | Suskind et al. |
| 5,626,944 A | 5/1997 | Rasmussen |
| 5,628,097 A | 5/1997 | Benson et al. |
| 5,731,061 A | 3/1998 | Bezier |
| 5,733,628 A | 3/1998 | Pelkie |
| 5,762,643 A | 6/1998 | Ray et al. |
| 5,763,044 A | 6/1998 | Ahr et al. |
| 5,830,555 A | 11/1998 | Srinivasan et al. |
| 5,914,084 A | 6/1999 | Benson et al. |
| 5,916,661 A | 6/1999 | Benson et al. |
| 5,919,177 A | 7/1999 | Georger et al. |
| 5,998,696 A | 12/1999 | Schone |
| 6,103,953 A | 8/2000 | Cree et al. |
| 6,114,263 A | 9/2000 | Benson et al. |
| 6,114,595 A | 9/2000 | Moore et al. |
| D431,369 S | 10/2000 | Thomas |
| 6,171,682 B1 | 1/2001 | Raidel et al. |
| 6,242,074 B1 | 6/2001 | Thomas |
| 6,383,431 B1 | 5/2002 | Dobrin et al. |
| 6,410,823 B1 | 6/2002 | Daley et al. |
| 6,436,082 B1 | 8/2002 | Mizutani et al. |
| 6,476,289 B1 | 11/2002 | Buell et al. |
| 6,506,329 B1 | 1/2003 | Curro et al. |
| 6,849,319 B2 | 2/2005 | Cree et al. |
| 6,989,187 B2 | 1/2006 | Thomas |
| 7,198,836 B2 | 4/2007 | Thomas |
| 7,351,297 B2 | 4/2008 | Middlesworth et al. |
| D696,029 S | 12/2013 | Seyler |
| D747,885 S | 1/2016 | Seyler |
| 10,258,517 B1 | 4/2019 | Maschino et al. |
| 2002/0016122 A1* | 2/2002 | Curro ............... B29C 55/18 442/381 |
| 2002/0062113 A1 | 5/2002 | Thomas et al. |
| 2002/0119720 A1 | 8/2002 | Arora et al. |
| 2003/0028165 A1 | 2/2003 | Curro et al. |
| 2003/0097113 A1 | 5/2003 | Molee |
| 2003/0105446 A1 | 6/2003 | Hutson et al. |
| 2003/0124311 A1 | 7/2003 | Cree et al. |
| 2003/0181120 A1 | 9/2003 | Wu et al. |
| 2003/0186026 A1 | 10/2003 | Thomas |
| 2003/0195487 A1 | 10/2003 | Thomas |
| 2004/0019340 A1 | 1/2004 | McBride |
| 2004/0087927 A1 | 5/2004 | Suzuki |
| 2004/0170810 A1 | 9/2004 | Rasmussen |
| 2004/0241389 A1 | 12/2004 | Chung et al. |
| 2005/0064136 A1* | 3/2005 | Turner ............... B26F 1/18 428/131 |
| 2005/0101216 A1 | 5/2005 | Middlesworth et al. |
| 2005/0261649 A1 | 11/2005 | Cohen |
| 2005/0267429 A1 | 12/2005 | Cohen |
| 2006/0013999 A1 | 1/2006 | Deep et al. |
| 2006/0062963 A1 | 3/2006 | Middlesworth et al. |
| 2007/0020434 A1 | 1/2007 | Thomas |
| 2007/0031636 A1 | 2/2007 | Tribble et al. |
| 2007/0105472 A1 | 5/2007 | Marche |
| 2007/0212545 A1 | 9/2007 | Cree et al. |
| 2008/0063837 A1 | 3/2008 | Pansy et al. |
| 2008/0216937 A1 | 9/2008 | Middlesworth et al. |
| 2009/0208703 A1 | 8/2009 | Wennerback et al. |
| 2010/0121298 A1 | 5/2010 | Seyler et al. |
| 2010/0201024 A1 | 8/2010 | Gibson et al. |
| 2010/0297387 A1 | 11/2010 | Rasmussen |
| 2011/0183109 A1 | 7/2011 | Seyler et al. |
| 2011/0184370 A1 | 7/2011 | Seyler et al. |
| 2012/0276331 A1 | 11/2012 | Orr et al. |

(56) References Cited

U.S. PATENT DOCUMENTS

| | | |
|---|---|---|
| 2012/0277710 A1 | 11/2012 | Marinelli et al. |
| 2012/0282436 A1 | 11/2012 | Coe et al. |
| 2015/0273793 A1 | 10/2015 | Thomas |

FOREIGN PATENT DOCUMENTS

| | | | |
|---|---|---|---|
| CN | 101754734 B | | 6/2010 |
| CN | 102470542 A | | 5/2012 |
| CN | 105208988 A | | 12/2015 |
| DE | 10008827 A1 | | 9/2001 |
| EP | 0403187 A1 | | 12/1990 |
| EP | 1500384 A2 | | 1/2005 |
| EP | 1990188 A2 | | 11/2008 |
| FR | 2759389 A1 | | 8/1998 |
| JP | H02193663 A | | 7/1990 |
| JP | 2004098356 A | * | 4/2004 |
| JP | 2008061691 A | * | 3/2008 |
| JP | 2008245959 A | | 10/2008 |
| WO | 9111161 A1 | | 8/1991 |
| WO | 9702133 A2 | | 1/1997 |
| WO | 9816177 A1 | | 4/1998 |
| WO | 9825759 A1 | | 6/1998 |
| WO | 0037249 A1 | | 6/2000 |
| WO | 2008051548 A2 | | 5/2008 |
| WO | 2011075669 A2 | | 6/2011 |

OTHER PUBLICATIONS

Machine Translation of JP-2008061691-A, Mar. 2008 (Year: 2008).*
International Preliminary Report on Patentability dated Sep. 26, 2019, for International Patent Application No. PCT/US2018/022002.
International Search Report and Written Opinion dated Jul. 6, 2018, for International Patent Application No. PCT/20181022002.
United States Statutory Invention Registration No. US H1670, published Jul. 1, 1997, Aziz, et al., "Absorbent Article Having a Nonwoven and Apertured Film Coversheet".
Indian Office Action dated Sep. 25, 2020, for Indian Patent Application No. 201917037627.
Chinese Office Action dated Apr. 26, 2021, for Chinese Patent Application No. 201880025145.3.

* cited by examiner

METHOD OF MANUFACTURING AN ACTIVATED COMPOSITE WEB AND AN ACTIVATED COMPOSITE WEB FOR ABSORPTIVE DEVICES

CROSS-REFERENCE TO RELATED APPLICATIONS

This application is a continuation of U.S. patent application Ser. No. 15/918,803, filed on Mar. 12, 2018, which claims the benefit of priority from U.S. Provisional Patent Application Ser. No. 62/470,671, filed Mar. 13, 2017, the entire contents of both of which are incorporated herein by reference.

FIELD

The present invention is related to an activated composite web that may be used in an absorptive device, and methods for making the activated composite web.

BACKGROUND

Plastic formed films and nonwovens are used as topsheets in absorptive devices such as feminine hygiene products, adult incontinence products, and baby diapers, for example. A topsheet is a top layer of the absorptive device that contacts the skin of the user (wearer) of the absorptive device. Nonwoven materials are often used as topsheet components of such absorptive devices where it is desirable to achieve softness due to the contact of the topsheet with the skin of the wearer of the absorptive device. Although a ratio of high loft to total thickness of the nonwoven material is often perceived to be soft and cool when used against the skin, special processing is typically needed to achieve such characteristics, which may increase the cost of the product.

For topsheets that are made from a formed film, it is desirable to have the visual appearance and softness of a soft cloth, instead of a stiff plastic film. Although topsheets that are made from plastic films typically have better performance characteristics when used in the absorptive device as compared to topsheets that are made from nonwoven materials, a topsheet made from a plastic film may have a visual appearance that is higher in gloss and therefore may be more "plastic-looking" than a nonwoven topsheet. Additionally, a plastic film topsheet may feel more "sticky" or "tacky" to the wearer than a nonwoven topsheet.

It is desirable to have a lightweight web that may be used in an absorptive device as, for example, a topsheet that has the performance attributes associated with a formed film and softness attributes associated with a nonwoven material.

SUMMARY

According to one non-limiting embodiment, the present invention provides a method of manufacturing an activated composite web. The method includes laminating a film layer to a nonwoven web to form a composite web, forming a plurality of apertured protuberances in the film layer with a pin punching unit, and passing the composite web through intermeshing elements to form an activated composite web. The intermeshing elements are constructed and arranged to form a plurality of first lanes substantially unaffected by activation aligned in a first direction and having a first width in a second direction substantially perpendicular to the first direction and also to form a plurality of second lanes aligned in the first direction and having a second width less than the first width in the second direction in the activated composite web. A first portion of the plurality of apertured protuberances forms a plurality of first apertured protuberances having a plurality of corresponding first apertures with first cross-sectional areas. The first apertured protuberances are located in the first lanes. A second portion of the plurality of apertured protuberances forms a plurality of second apertured protuberances having a plurality of corresponding second apertures with second cross-sectional areas, each of the second cross-sectional areas being larger than each of the first cross-sectional areas. The second apertured protuberances are located in the second lanes. Each of the first apertures has a first major axis substantially aligned in the first direction. Each of the second apertures has a second major axis substantially aligned in the second direction.

In another embodiment of the method, the film layer has a basis weight of between about 6 gsm and about 20 gsm.

Still further, it is contemplated that the method may be provided such that the nonwoven web has a basis weight of between about 8 gsm and about 18 gsm.

The method also may provide so that the plurality of apertured protuberances are arranged in a pattern having a mesh count of at least 35.

In another non-limiting embodiment, the present invention provides an activated composite web, that includes a composite web having a nonwoven layer and a film layer attached to the nonwoven layer. The film layer includes a plurality of apertured protuberances. The composite web is activated by stretching with intermeshing elements to form the activated composite web. The activated composite web has a plurality of first lanes substantially unaffected by activation aligned in a first direction and a first width in a second direction substantially perpendicular to the first direction. A first portion of the plurality of apertured protuberances forms a plurality of first apertured protuberances having a plurality of corresponding first apertures with first cross-sectional areas, the first apertured protuberances located in the first lanes. The activated composite web also has a plurality of second lanes aligned in the first direction and a second width less than the first width in the second direction. The first lanes and the second lanes alternate with each other in the second direction. A second portion of the plurality of apertured protuberances forms a plurality of second apertured protuberances having a plurality of corresponding second apertures with second cross-sectional areas, each of the second cross-sectional areas being larger than each of the first cross-sectional areas. The second apertured protuberances are located in the second lanes. Each of the first apertures has a first major axis substantially aligned in the first direction. Each of the second apertures has a second major axis substantially aligned in the second direction.

In one further contemplated embodiment of the activated composite web according to the present invention, the film layer has a basis weight of between about 6 gsm and about 20 gsm.

It is contemplated that the activated composite web may be constructed where the nonwoven web has a basis weight of between about 8 gsm and about 18 gsm.

Still further, in the activated composite web according to the present invention, the plurality of apertured protuberances are arranged in a pattern having a mesh count of at least 35.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Figure 1:
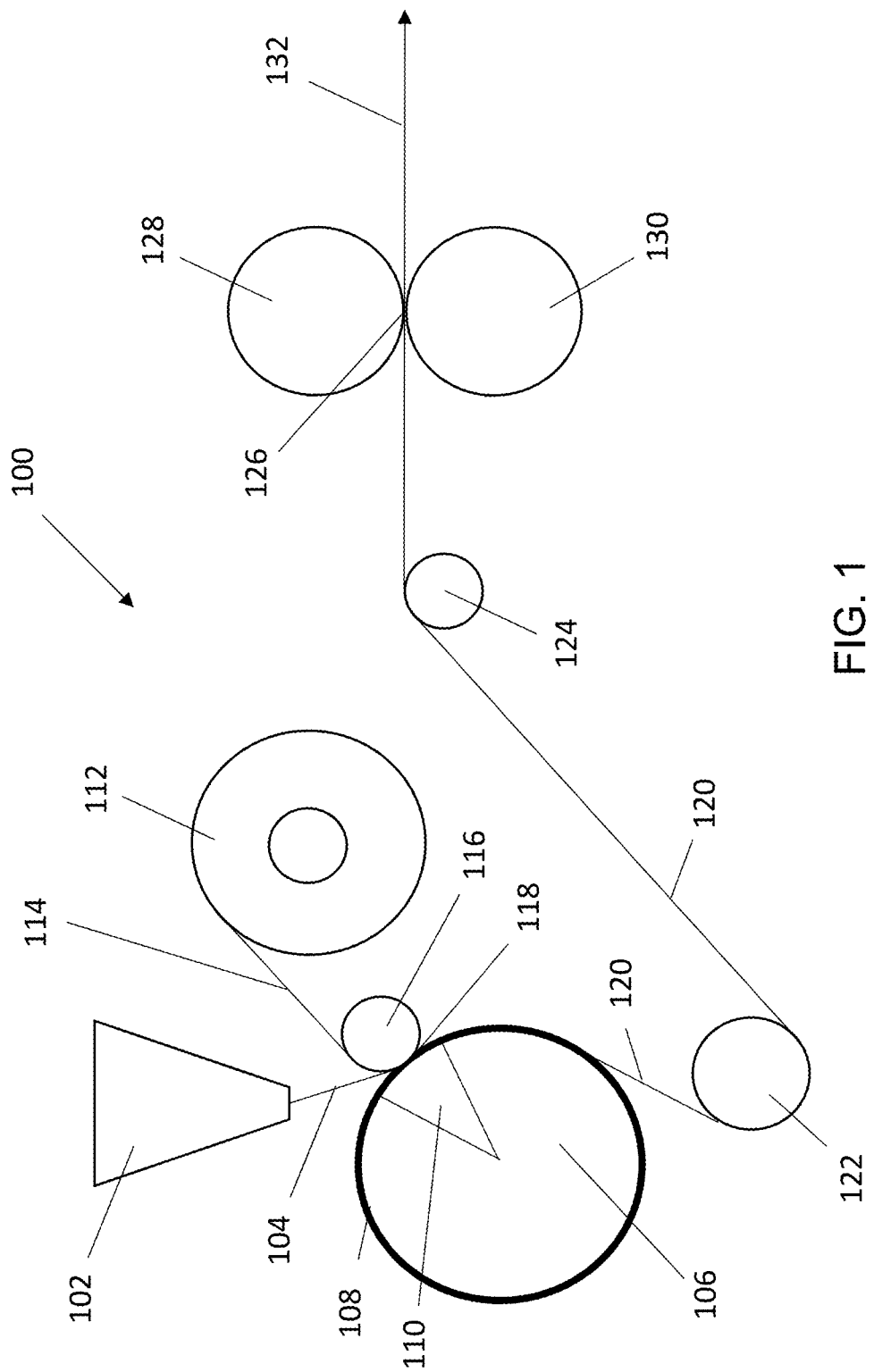
FIG. 1 is a schematic representation of an apparatus for manufacturing an activated, lightweight, composite web according to embodiments of the invention.

Throughout this description, the term "web" refers to a material capable of being wound into a roll. Webs can be film webs, nonwoven webs, laminate webs, apertured laminate webs, etc. The face of a web refers to one of its two dimensional surfaces, as opposed to its edge. The term "composite web" refers to a web that comprises two or more separate webs that are attached to each other in a face to face relationship. The attachment can be through the edges of the component webs, although the component webs lie in a face to face relationship with each other, or the attachment can be at particular locations across the component webs.

The term "film" in this description refers to a web made by extruding a molten sheet of thermoplastic polymeric material by a cast or blown extrusion process and then cooling said sheet to form a solid polymeric web. Films can be monolayer films, coextruded films, coated films, and composite films. Coated films are films comprising a monolayer or coextruded film that are subsequently coated (for example, extrusion coated, impression coated, printed, or the like) with a thin layer of the same or different material to which it is bonded. Composite films are films comprising more than one film where the at least two films are combined in a bonding process. Bonding processes may incorporate adhesive layers between the film layers.

Throughout this description, the expression "apertured films" denotes films in which there exist a plurality of holes that extend from one surface to a second surface. A two dimensional apertured film is a film in which no three dimensional structure exists in the holes, which then connect the second surface of a flat film to the first surface of the film. A "formed film" is a three dimensional film with protuberances, and a three dimensional apertured film is a film in which a three dimensional structure exists in the apertures (e.g., the apertures have a depth that is thicker than the thickness of the film) or the protuberances have apertures therethrough.

The term "nonwoven" means a web comprising a plurality of fibers. The fibers may be bonded to each other or may be unbonded. The fibers may be staple fibers or continuous fibers. The fibers may comprise a single material or may comprise a multitude of materials, either as a combination of different fibers or as a combination of similar fibers each comprised of different materials. As used herein, "nonwoven web" is used in its generic sense to define a generally planar structure that is relatively flat, flexible and porous, and includes staple fibers or continuous filaments. The nonwoven web may be the product of any process for forming the same, such as nonwoven spunbond and melt blown nonwoven webs. The nonwoven web may include a composite or combination of webs. In an embodiment, the nonwoven web is a spunbond material, made of polypropylene fiber. The nonwoven web may, however, comprise any polymeric material from which a fiber can be produced and/or may comprise cotton or other natural fibers. For example, the nonwoven web may comprise fibers of polyethylene, polypropylene, elastomers, polyesters, rayon, cellulose, nylon, cotton (or other natural fibers), and blends of such fibers. Fibers that comprise different polymers may also be blended.

The term "extensibility" as used herein refers to the maximum amount of strain (in %, relative to the zero strain state) that can be applied to a web in a given direction by a tensile force without breakage of fibers, or bonds between fibers. For a nonwoven web to be extensible in any given direction means that when a tensile force is applied to the web in that direction, the web expands in that direction, and a strain is induced in the web, substantially without breakage of fibers, or of bonds between fibers.

The term "screen" as used herein refers to a three-dimensional molding apparatus comprising indentations and/or apertures and/or protrusions used to form protuberances or apertures in films. In an embodiment, screens comprise tubular members, having a width and a diameter. In alternative embodiments, screens comprise belts having a width and a length. The transverse direction is the direction parallel to the width of the screen. The machine direction is the direction parallel to the direction of rotation of the screen, and is perpendicular to the transverse direction.

The term "protuberance" as used herein refers to a three-dimensional member comprising an apertured base portion located in the plane of the first surface of the film and a sidewall portion extending generally in the direction of the second surface of the film. Each base portion has a sidewall portion. Sidewall portions terminate in "ends" located in the plane of the second surface of the film. The ends of the protuberances may be apertured or unapertured. "Apertured protuberance" as used herein refers to a protuberance that has an aperture at its end in the plane of the second surface.

The apertures in the base portions of the protuberances, also called "primary apertures," may be in the shape of polygons, for example squares, hexagons, pentagons, ellipses, circles, ovals, or slots, in a regulated or random pattern. In an embodiment, the apertures may be in the shape of a boat, as described in, for example, U.S. Pat. No. 7,198,836, which is incorporated herein by reference. The protubered ends, if apertured, are called "secondary apertures," and may be in the shape of polygons, e.g., squares, hexagons, pentagons, ellipses, circles, ovals, slots, or boats.

As used herein, the expression "absorbent articles" and "absorptive devices" denote articles that absorb and contain body fluids and other body exudates. More specifically, an absorbent article/absorptive device includes garments that are placed against or in proximity to the body of a wearer to absorb and contain the various exudates discharged from a body.

As used herein, the term "activating" or "activation" refers to a process of stretching a material beyond a point where its physical properties are changed. In the case of a nonwoven web, sufficient activation of the web will result in the nonwoven web being more extensible and/or improving its tactile properties. In an activation process, forces are applied to a material causing the material to stretch. Formed film and nonwoven webs may be mechanically activated, for example. Mechanical activation processes comprise the use of a machine or apparatus to apply forces to the web to cause stretching of the web. Methods and apparatus used for activating webs of materials include, but are not limited to, activating the web through intermeshing gears or plates, activating the web through incremental stretching, activating the web by ring rolling, activating the web by tenter frame stretching, canted wheel stretchers or bow rollers, and activating the web in the machine direction between nips or roll stacks operating at different speeds to mechanically stretch the components, and combinations thereof.

Referring now to FIG. 1, FIG. 1 illustrates an apparatus 100 that may be used to manufacture an activated, lightweight, composite web according to embodiments of the present invention. As illustrated, the apparatus 100 includes an extrusion die 102 constructed and arranged to extrude a polymer melt curtain (molten polymer web) 104 onto vacuum forming cylinder 106. In an embodiment, the molten polymer web 104 may include a polyolefin selected from the group consisting of polyethylene, polypropylene, ethylene-vinyl acetate, and a metallocene-based polyolefin. The polyethylene may be selected from the group consisting of ultra low density polyethylene, linear low density polyethylene, and linear medium density polyethylene. In an embodiment, the molten polymer web 104 may include an elastomeric polymer selected from the group consisting of polypropylene based elastomers, ethylene based elastomers, copolyester based elastomers, olefin block copolymers, and styrenic block copolymers.

The vacuum forming cylinder 106 includes a forming screen 108 and a vacuum slot 110. A supply roll 112 of a nonwoven web 114 is provided on a spindle in a position that allows the nonwoven web 114 to be fed onto a laminating roller 116 located adjacent to the vacuum forming cylinder 106. As the nonwoven web 114 rotates around the laminating roller 116 and into a nip 118 between the laminating roller 116 and the vacuum forming cylinder 106, the nonwoven web 114 contacts the polymer melt curtain 104 while the polymer is still molten at an impingement point between the forming screen 108 of the vacuum forming cylinder 106 and the laminating roller 116. Desirably, the impingement point is directly over the leading edge of the vacuum seal at the vacuum slot 110 of the vacuum forming cylinder 106.

The pattern of apertures in the forming screen 108 determines the pattern of protuberances in the formed film. In an embodiment of the invention, the formed film layer includes a pattern of apertured protuberances having a mesh count of 57 (i.e. 57 apertures per linear inch), with each apertured protuberance having a cross-section in the shape of a boat (i.e. a boat shaped cell or "BSC"). Such a pattern may be referred to as "57 BSC." The boat shaped cell-type aperture is described in further detail in U.S. Pat. No. 6,989,187, which is incorporated herein by reference. Other formed film aperture patterns that are well known in the formed film art may also be useful, such as hexagon, square, or round apertures having mesh counts of, for example, 100, 80, 60 or 40 apertures per linear inch. Patterns with a mesh count of 30 or less may lose the sensation of softness and may not respond well to activation, which is described in further detail below.

In an embodiment, the formed film layer has a plurality of apertured protuberances having a mesh count of at least 35. In an embodiment, the apertured protuberances have a mesh count of at least 40. In an embodiment, the apertured protuberances have a mesh count of at least 45. In an embodiment, the apertured protuberances have a mesh count of at least 50. In an embodiment, the apertured protuberances have a mesh count of at least 55. In an embodiment, the apertured protuberances have a mesh count of at least 60. In an embodiment, the apertured protuberances have a mesh count of at least 65. In an embodiment, the apertured protuberances have a mesh count of at least 70. In an embodiment, the apertured protuberances have a mesh count of at least 75. In an embodiment, the apertured protuberances have a mesh count of at least 80. In an embodiment, the apertured protuberances have a mesh count of at least 85. In an embodiment the apertured protuberances have a mesh count of at least 90. In an embodiment, the apertured protuberances have a mesh count of at least 95. In an embodiment, the apertured protuberances have a mesh count of at least 100.

The fibrous web material of the nonwoven web 114 embeds partially into the molten polymer web 104 to create a formed laminate web 120. The two webs 104, 114 continue on over the vacuum slot 110 as apertured protuberances, described in further detail below, are formed in the molten polymer web 104. Air flow is initiated through the apertures in the forming screen 108, which cools and solidifies the molten polymer web 104 and, by becoming solid, the polymer web traps embedded fibers from the nonwoven web 114, thereby bonding the nonwoven web 114 to what is now a formed film layer to form the vacuum formed laminate web 120.

The formed film layer may have a basis weight of between about 6 gsm and about 20 gsm. In an embodiment, the formed film layer has a basis weight of about 6 gsm. In an embodiment, the formed film layer has a basis weight of about 7 gsm. In an embodiment, the formed film layer has a basis weight of about 8 gsm. In an embodiment, the formed film layer has a basis weight of about 9 gsm. In an embodiment, the formed film layer has a basis weight of about 10 gsm. In an embodiment, the formed film layer has a basis weight of about 11 gsm. In an embodiment, the formed film layer has a basis weight of about 12 gsm. In an embodiment, the formed film layer has a basis weight of about 13 gsm. In an embodiment, the formed film layer has a basis weight of about 14 gsm. In an embodiment, the formed film layer has a basis weight of about 15 gsm. In an embodiment, the formed film layer has a basis weight of about 16 gsm. In an embodiment, the formed film layer has a basis weight of about 17 gsm. In an embodiment, the formed film layer has a basis weight of about 18 gsm. In an embodiment, the formed film layer has a basis weight of about 19 gsm. In an embodiment, the formed film layer has a basis weight of about 20 gsm.

The nonwoven web may have a basis weight of between about 8 gsm and about 18 gsm. In an embodiment, the nonwoven web has a basis weight of about 8 gsm. In an embodiment, the nonwoven web has a basis weight of about 9 gsm. In an embodiment, the nonwoven web has a basis weight of about 10 gsm. In an embodiment, the nonwoven web has a basis weight of about 11 gsm. In an embodiment, the nonwoven web has a basis weight of about 12 gsm. In an embodiment, the nonwoven web has a basis weight of about 13 gsm. In an embodiment, the nonwoven web has a basis weight of about 14 gsm. In an embodiment, the nonwoven web has a basis weight of about 15 gsm. In an embodiment, the nonwoven web has a basis weight of about 16 gsm. In an embodiment, the nonwoven web has a basis weight of about 17 gsm. In an embodiment, the nonwoven web has a basis weight of about 18 gsm.

Returning to FIG. 1, the vacuum formed laminate web 120 is pulled off of the vacuum forming cylinder 106 by a peel roll 122 and proceeds to travel in a machine direction over an idle roll 124 and is introduced into an activation nip 126. The activation nip 126 is formed when a first intermeshing gear roller 128 is engaged with a second intermeshing gear roller 130 at a depth of engagement. The activation may be carried out in the machine direction (MD) or in the transverse direction (TD) relative to the direction of motion of the activated, lightweight, composite web 132.

Figure 2:
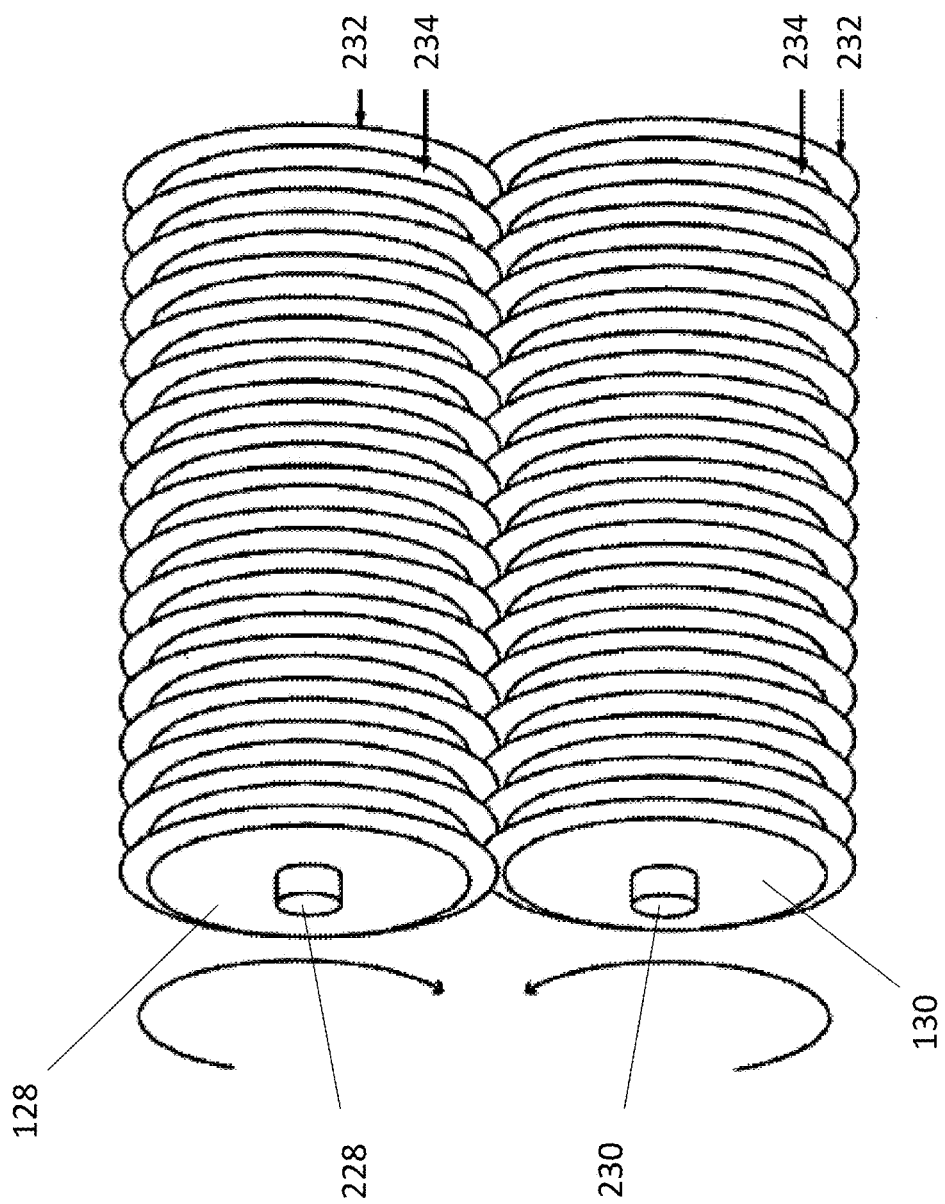
FIG. 2 is a schematic representation of a portion of the apparatus illustrated in FIG. 1 according to embodiments of the invention.

FIG. 2 illustrates an embodiment of the intermeshing gear ("IMG") rollers 128, 130 that may be used in the apparatus 100 of FIG. 1 for TD activation. As illustrated, the rollers 128, 130 are carried on respective rotatable shafts 228 and 230, having their axes of rotation disposed in parallel relationship. Each of rollers 128, 130 includes a plurality of axially-spaced, side-by-side, circumferentially-extending, equally-configured gears 232 that can be in the form of thin fins of substantially rectangular cross section.

The spaces between adjacent gears 232 define recessed, circumferentially-extending, equally configured grooves 234. Without limiting the present invention, the gears 232 also are referred to as "teeth 232" herein. The grooves 234 can be of substantially rectangular cross section when the gears 232 are of substantially rectangular cross section. Thus, each of forming rolls 128, 130 includes a plurality of spaced gears 232 and alternating grooves 234 between each pair of adjacent gears 232. The gears 232 and the grooves 234 need not each be of the same width, however, and preferably, the grooves 234 have a larger width than that of the gears 232, to permit the material that passes between the forming rolls 128, 130 to be received within the respective grooves 234 and to be locally stretched. The vacuum formed laminate web 120 uniquely responds to this stress, which results in the forming of an activated, lightweight, composite web 132 according to the present invention.

In MD activation, a view of the cross section of the forming rolls 128, 130 looking down the axes of the rotatable shafts 228, 230 of the forming rolls 128, 130 would show gear teeth (not shown) cut into and around the circumference of the forming rolls 128, 130, with their long axes substantially parallel with the axes of the forming rolls 128, 130. The teeth on one forming roll 128 meshes into the grooves on the adjacent roll 130 in order to provide a stretching action to the web 120.

The depth of engagement of the roller teeth, gears, or fins 232 determines the degree of elongation to which the vacuum formed laminate web 120 is subjected. A balance usually is drawn between the depth of engagement of the roller teeth 232 and the composition of the vacuum formed laminate web 120, as these affect many important physical properties of the activated, lightweight, composite web 132. Some of the factors affecting the choice of pitch, teeth depth, and depth of engagement include the composition of the activated, lightweight, composite web 132, desired final properties (breathability, absorbency, strength, cloth-feel), and the width and diameter of the IMG rollers 128, 130. The final application of the activated, lightweight, composite web 132 also affects these choices because it determines desired final properties. The width of the IMG rollers 128, 130 may present economic and technical limitations. In particular, as the width increases, the weight of the IMG rollers 128, 130 also increases, as does the amount of deflection experienced by the IMG rollers 128, 130. Deflection creates variation not only in the process of stretching, but also in the process of making the IMG rollers 128, 130, particularly as the pitch and tooth depth increases. Those skilled in the art are capable of varying the parameters of the IMG rollers 128, 130 to achieve the desired stretching, using the guidelines provided herein.

Returning to FIG. 1, the vacuum formed laminate web 120 is activated in the activation nip 126 by the IMG rollers 128, 130 to form the activated, lightweight, composite web 132, which may be introduced to further downstream steps such as adding treatment, slitting and winding of rolls, and the like, as desired for the end product.

Figure 3:
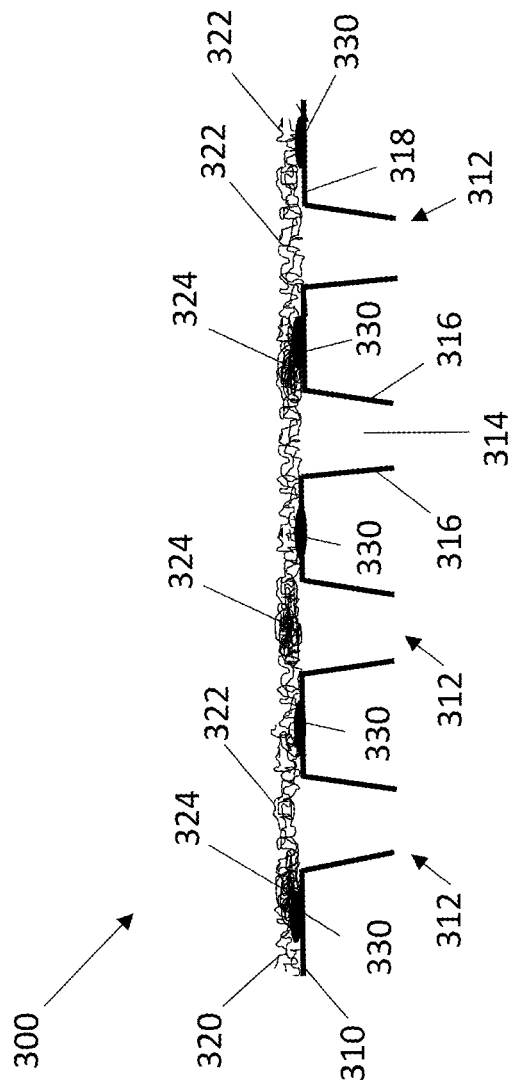
FIG. 3 is a schematic representation of a cross-section of a portion of an activated, lightweight, composite web according to embodiments of the invention.

FIG. 3 illustrates a schematic cross-section of a portion of a lightweight composite web 300 in accordance with embodiments of the invention. As illustrated, the lightweight composite web 300 includes a formed film layer 310 and a nonwoven layer 320. The cross-section illustrated is taken from a wide lane portion, which is described in further detail below, of the lightweight composite web 300. The formed film layer 310 includes a plurality of apertured protuberances 312 that extend away from the nonwoven layer 320. In an embodiment, the formed film layer 310 may be oriented so that the apertured protuberances 312 extend towards the nonwoven layer 320. The orientation of the apertured protuberances 312 may be left to the discretion of the absorptive device designer. Each apertured protuberance 312 includes an aperture 314 that is surrounded by sidewalls 316 crowning at lands 318 that extend in between the apertures 314 of adjacent protuberances 312. The lands 318 may be planar or slightly curved and the size of the lands 318 may range from a measurable distance between apertures 314 to being very sharp and razor-like with negligible distance.

The formed film layer 310 is attached to the nonwoven layer 320 at a plurality of fusion bond points 330 generally located at the lands 318 of the formed film layer 310 so that the composite web 300 is laminated with sufficient peel force for keeping the layers 310, 320 attached during later conversion methods and ultimately during use where applied stresses might tend to cause layer separation. A vacuum forming lamination method for causing this fusion bond 330 is described in further detail in U.S. Pat. No. 6,242,074, which is incorporated herein by reference.

In an embodiment, additional apertures may be formed through the composite web 300 either before or after activation via any suitable means. For example, in an embodiment, a pin punching unit, such as the pin punching unit described in, for example U.S. Pat. No. 6,849,319, which is incorporated herein by reference, may be positioned in between the vacuum cylinder 106 and the IMG rollers 128, 130, or after the IMG rollers 128, 130, depending on the desired effect. Such additional apertures may be arranged in a pattern having a mesh count of less than 35 apertures per linear inch, for example. In an embodiment, a pin punching unit may be used in lieu of the vacuum cylinder 106 and forming screen 108 to form the plurality of apertured protuberances 312, after a film layer has been laminated to the nonwoven web.

Figure 4:
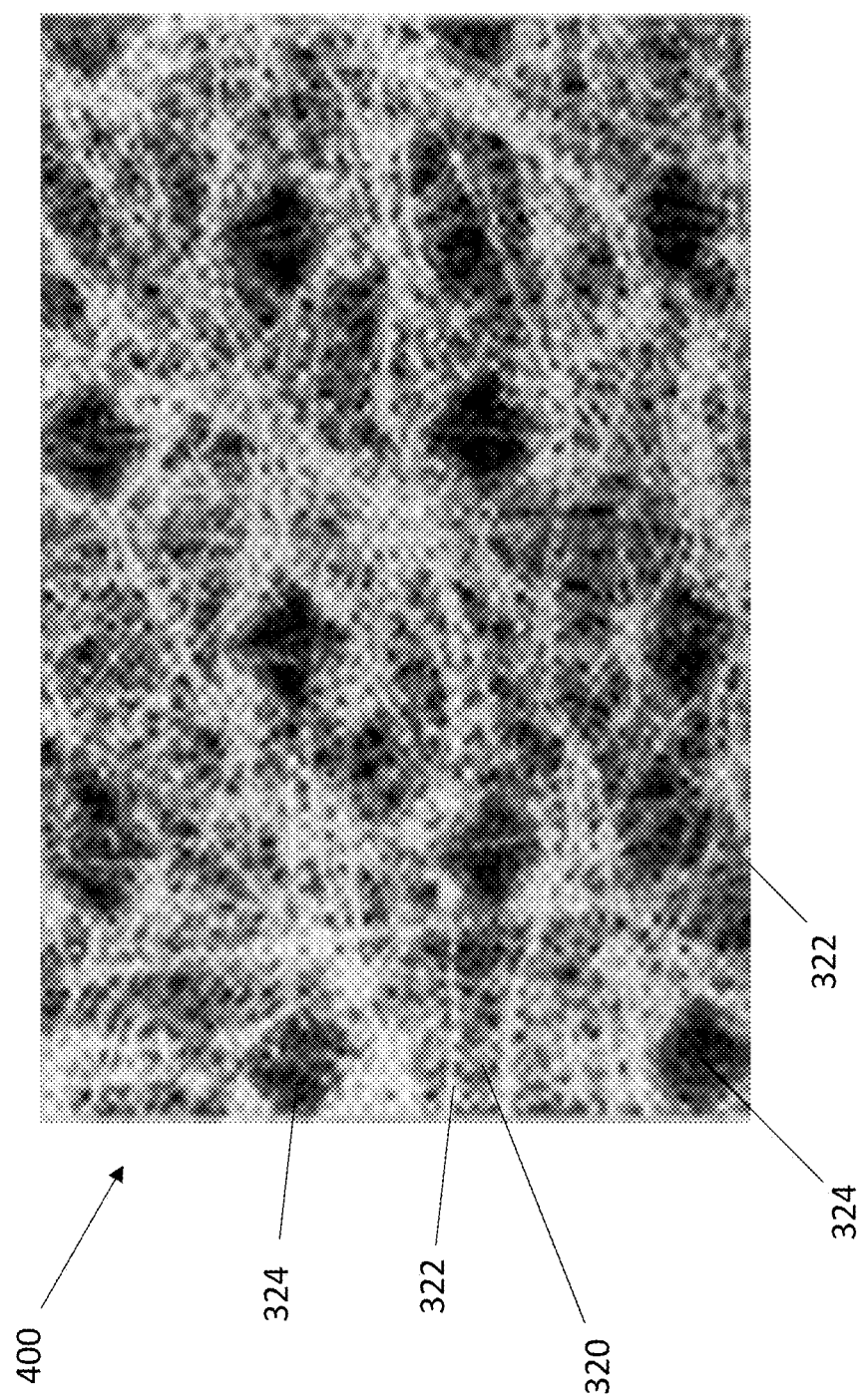
FIG. 4 is a photograph of one side of the activated, lightweight, composite web according to embodiments of the invention.

FIG. 4 is an enlarged photograph 400 of the side of the nonwoven layer 320 that faces away from the formed film layer 310, i.e., the outside face of the nonwoven layer 320. As illustrated in FIGS. 3 and 4, the nonwoven layer 320 includes a plurality of fibers 322 and a plurality of press-melted sites 324 that locally bond fibers together to form a web with a generally uniform thickness and integrity for the nonwoven layer 320. The fibers 322 are made from polymer, which may be a polyolefin, such as polypropylene.

Press-melted sites 324 are typical for a spun bond non-woven, such as the one of this embodiment. Without the press-melted sites 324, the fibers 322 would separate and fall away from each other, thereby taking away from the integrity of the nonwoven layer 320. The press-melted sites 324 may or may not be in register with the fusion bonds 330, as required or as desired. As is apparent from the embodiment illustrated in FIG. 3, the press-melted sites 324 are generally not in register with the fusion bonds 330.

U.S. Pat. No. 5,916,661, which is incorporated by reference, teaches that press-melted sites, such as the press-melted sites 324 illustrated in FIGS. 3 and 4, also thin and weaken the fibers in the area which melted together while under a pressure point. The press-melted sites may be formed with a patterned calendar roller and a smooth anvil roller which may be heated and the pressure between the two rollers may be adjusted to provide the desired temperature and pressure to concurrently weaken and melt-stabilize the nonwoven web at a plurality of these locations. This not only provides for web integrity with the pre-existing press-melted sites of any spun bond nonwoven, but more sites can be provided such that when activated with a pair of rollers with intermeshing gears the press-melted, weakened fibers break to form openings in the nonwoven. In this way, an activated nonwoven web with several openings existing at the press-melted sites may be formed.

Figure 5:
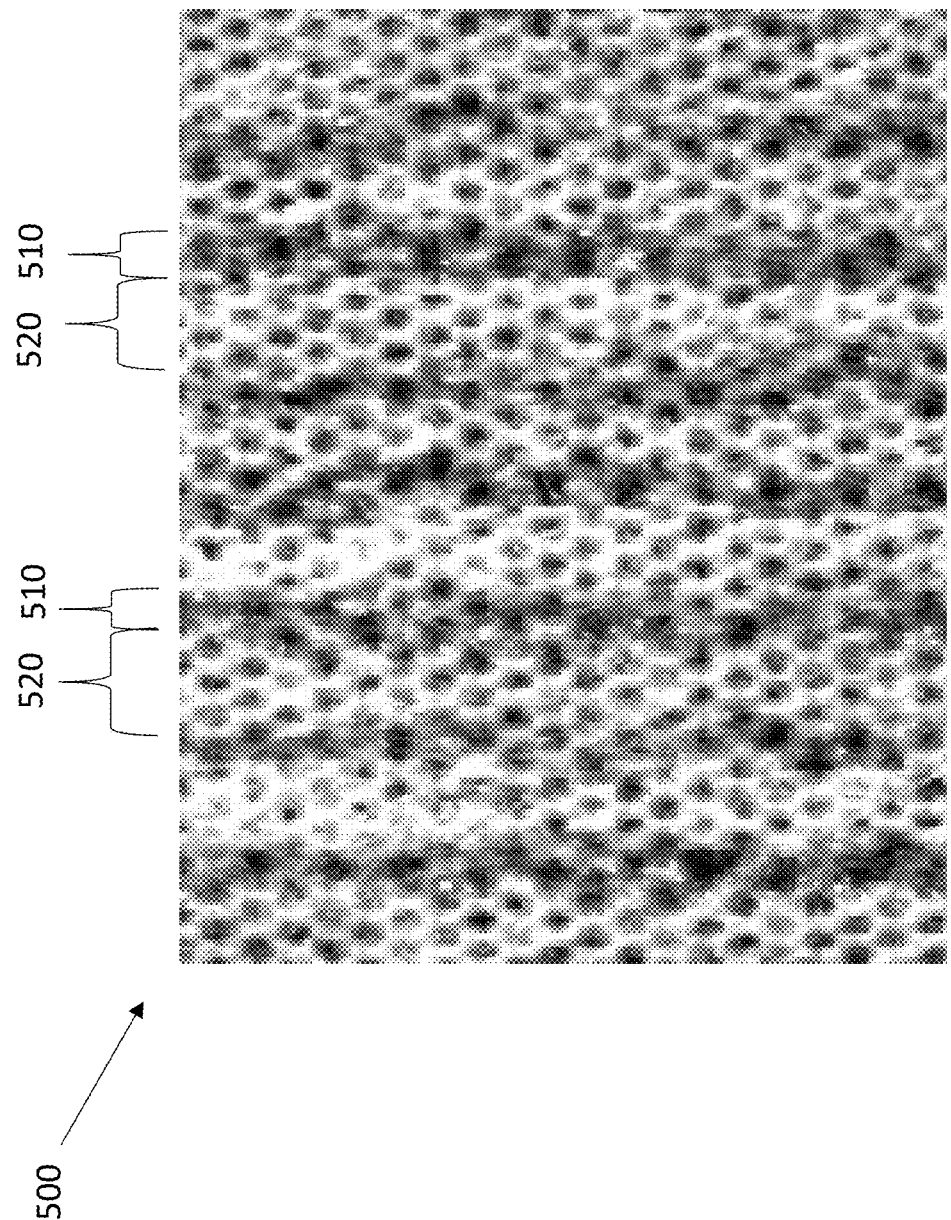
FIG. 5 is a photograph of one side of the activated, lightweight, composite web, opposite the side illustrated in FIG. 4, according to embodiments of the invention.

FIG. 5 is an enlarged photograph 500 showing the plan view of the composite web 300 with several narrow lanes 510 and several wide lanes 520. The wide lanes 520 are substantially comprised of a majority of smaller apertured protuberances 312, and the narrow lanes 510 are comprised of larger apertured protuberances 312. Generally, one or two apertured protuberances 312 in the narrow lanes 510 are enlarged. Wide lanes are typically three, and sometimes four, apertures 314 wide in this embodiment of the 57 BSC pattern. While the majority of apertures 314 in the wide lanes are unaffected by activation, a few random apertures 314 may become slightly larger. The lane widths and their spacing are primarily determined by the intermeshing gear spacing and gear width. This can be varied for affecting different lane widths for different mesh counts.

For this embodiment, the gears were spaced apart on centers at 0.105 inches, have a width of 0.043 inches, and a height of 0.260 inches. They are slightly tapered and have flat, squared tips. In this embodiment, the basis weight of the formed film layer before activation was about 11.7 g/m² (gsm). Combined with the 10 gsm nonwoven web, the sum of the original components of the formed film layer 310 and the nonwoven layer 320 before activation was about 21.7 gsm. However, the activated, lightweight, composite web 132 is lighter, at about 17.2 gsm. Therefore, the activated, lightweight, composite web 132 is lighter by about 20% than the sum of its original components. In the range of applicable basis weights for the formed film layer 310 and for the nonwoven layer 320, it is believed that most activated composite webs will be at least about 15% lighter to no more than about 25% lighter than the sum of their original components.

Most commonly, as with this embodiment, the narrow lanes 510 are aligned in the machine direction. In random spots, the narrow lanes 510 may have a wavy line for small segments along their length in the lightweight composite web 300. This does not harm their performance and may even add to the aesthetic value. Also, if desired, activation methods known in the art may be used to create a lightweight composite web 300 where the narrow lanes 510 are aligned in the cross direction.

Figure 6:
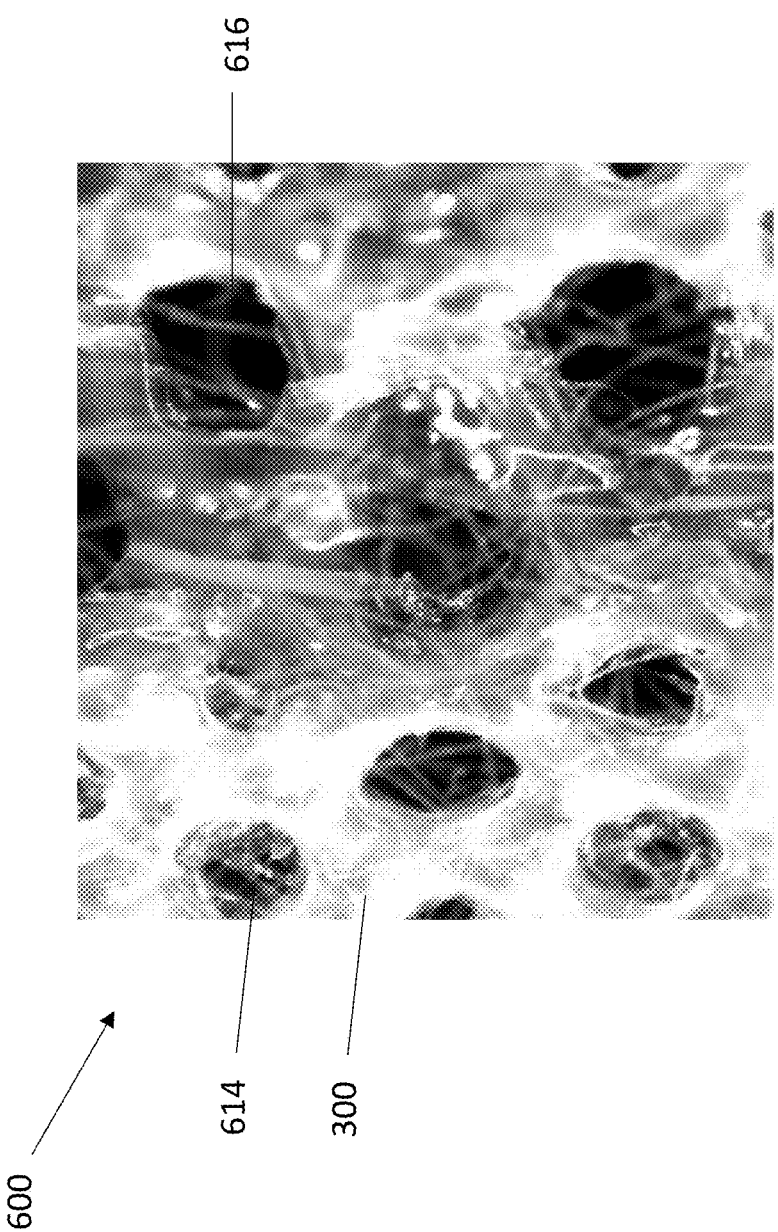
FIG. 6 is a photograph of a zoomed-in portion of the side of the activated, lightweight, composite web illustrated in FIG. 5.

Referring now to FIG. 6, a greater magnification photograph 600 of the lightweight composite web 300 is shown, focusing at just a few apertures 616 from a narrow lane 510 and a few apertures 614 from a wide lane 520.

Figure 7:
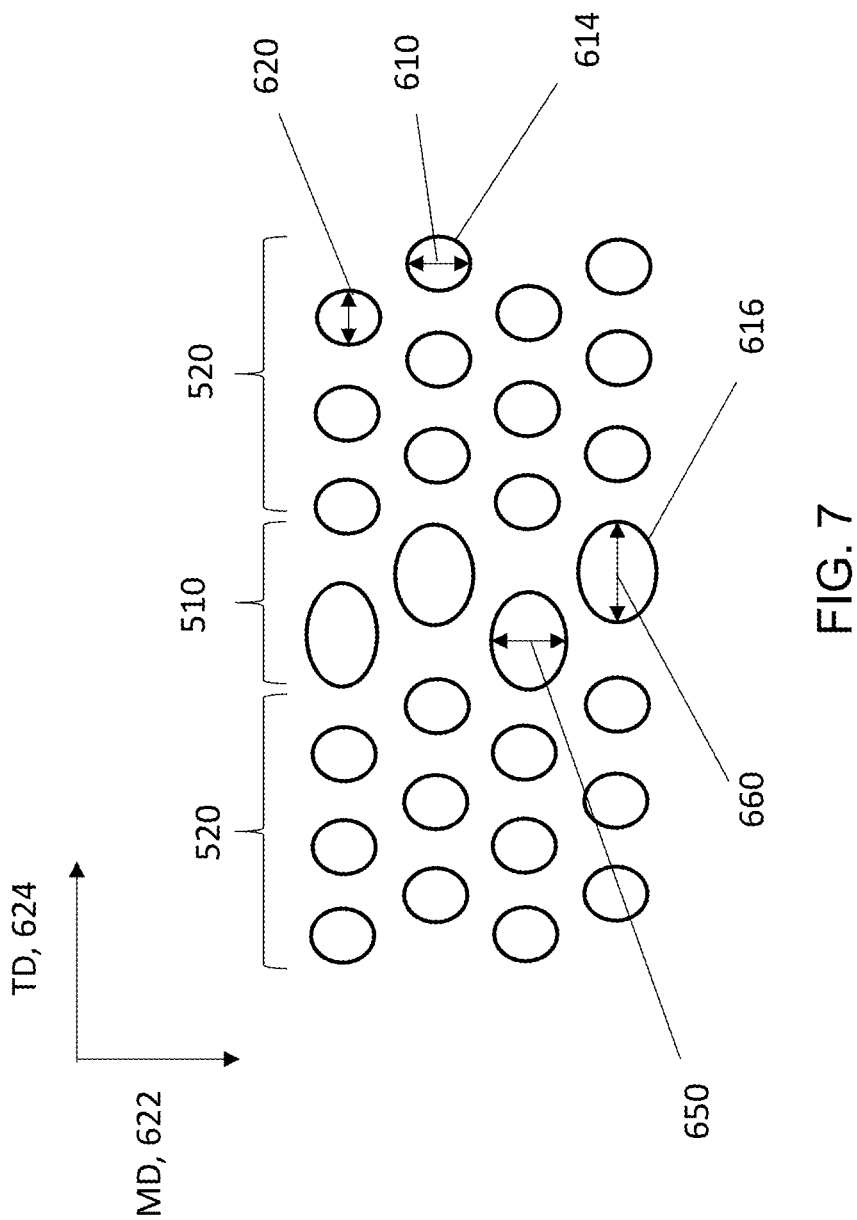
FIG. 7 is a schematic representation of the side of the activated, lightweight, composite web illustrated in FIG. 5.

FIG. 7 schematically illustrates a more uniform graphic that illustrates the differences between the apertures 614 in the wide lanes 520 and the apertures 616 in the narrow lanes. As illustrated, one narrow lane 510 is between two wide lanes 520. Within wide lanes 520 are smaller apertures 614 with a major axis 610 and a minor axis 620. In this graphic, the major axis 610 of the smaller apertures 614 is aligned in a first direction, vertically, along the machine direction (MD) axis 622. Within narrow lane 510 there are enlarged apertures 616 with a minor axis 650 and a major axis 660. In this graphic, the major axis 660 is reversed in orientation and is aligned in a second direction, horizontally, along the transverse direction (TD) axis 624.

As illustrated in FIG. 7, for this 57 BSC embodiment, each of the wide lane apertures 614 has a major axis 610 and a minor axis 620. Even if patterns of hexagons or circles were used, instead of a BSC pattern, when a formed film or a formed film composite is produced the machinery pulls the web downstream through a series of driven rollers and/or driven nipped rollers. To keep the web free from wrinkles it is necessary to have a slight increase in the speed of each subsequent driven roller system. This is called 'draw'. This machine direction draw will impart into the pattern of the aperture 314 some extension to the machine direction axis 622 and some narrowing to the transverse direction axis 624. Thus, whether or not an intended BSC pattern is utilized, the result will be wide lanes 520 where the smaller aperture 614 has a major axis 610 along the machine direction axis 622 and a minor axis 620 along the transverse direction axis 624. For this embodiment, the smaller aperture 614 in wide lane 520 has the major axis 610 aligned in the machine direction with a measurement of about 0.0080 inches and the minor axis 620 aligned in the transverse direction with a measurement of about 0.0045 inches.

Surprisingly, the apertures 616 in the narrow lanes 510 not only become enlarged but many of the enlarged apertures 616 have a reversed axis alignment. In this embodiment for example, the narrow lane's enlarged aperture 616 has a reversed axis orientation with the minor axis 650 aligned in the machine direction and the major axis 660 aligned in the transverse direction. The minor axis 650 of the enlarged apertures 616 of this embodiment, aligned in the machine direction, measures about 0.0075 inches. The major axis 660 of the enlarged apertures 616 of this embodiment, aligned in the cross direction, measures about 0.0100 inches. Thus, activation causes the effect where many of the narrow lane enlarged apertures 616 have a reversed axis compared to the smaller apertures 614 in the wide lane 520, with their major axis 610 in the transverse direction and their minor axis 620 in the machine direction.

The area of the apertures 314, 614, 616 is calculated as the area of an oval: ½ the major axis 610, 660 times ½ the minor axis 620, 650 times 3.14159 (Pi, π). For the wide lane's smaller aperture 614 of this embodiment of FIG. 5, that yields the equation: 0.004×0.00225×3.14159=0.0000283 square inches. For the narrow lane enlarged aperture 616 of this embodiment of FIG. 5, it yields the equation: 0.0050× 0.00375×3.14159=0.0000589 square inches. Therefore, the enlargement factor of the enlarged apertures 616 compared to the smaller apertures 614 is about 200%. For the range of patterns useful for this web, activation may cause an enlargement factor of at least about 150%.

Figure 8:
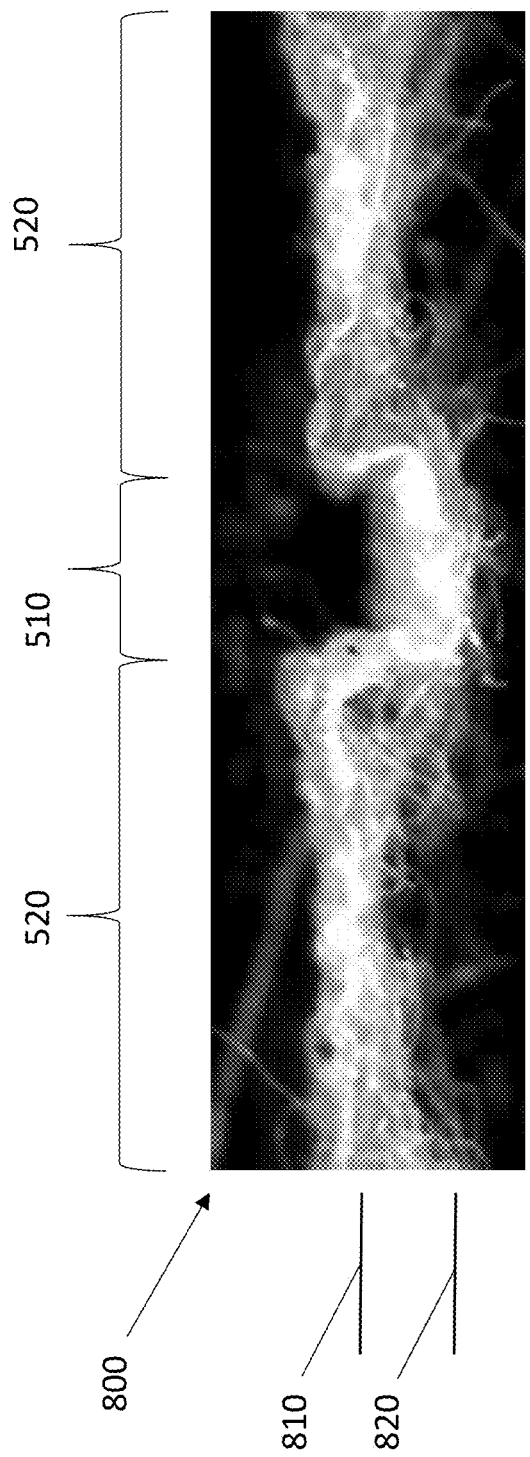
FIG. 8 is a photograph of a cross-section of the activated, lightweight, composite web of FIG. 5.

Referring now to FIG. 8, a magnified photograph 800 of the cross-section of the activated lightweight composite web 132 of the present invention is shown. Photograph 800 shows a single narrow lane 510 separating two wide lanes 520. Wide lanes 520 exist in a first plane 810 and narrow lanes 510 exists in a second plane 820, different from the first plane 810. The distance between the first plane 810 and the second plane 820 is varied and will generally depend on the depth of engagement of the intermeshing gears 228, 230 of the activation step and how a specific pattern of protuberances and polymer blend in the formed film layer responds to the activation stress. It will also depend, lane to lane, on the slight variations of thickness and homogeneity throughout a web with a common nonwoven and formed film pattern and polymer blend.

Another theoretical advantage of these lanes 510, 520 in different planes 810, 820 may be that it provides extra coolness and comfort. In a diaper, for example, as the baby urinates and the warm urine accumulates in the diaper core, warm, humid moisture vapors can develop. If these vapors cannot escape fairly quickly, the diaper may become clammy and uncomfortable. Having narrow lanes 510 in the second plane 820 may provide a lateral or longitudinal void space as a pathway for moisture vapor escape. This concept is described in U.S. Patent Application Publication No. 2003/0195487, which is incorporated herein by reference, and provides some data for an enhanced cooling rate if a void space is provided. Thus, it is believed that the activated, lightweight, composite web 132 of the present invention has a feature that provides some void space for an enhanced cooling rate.

Figure 9:
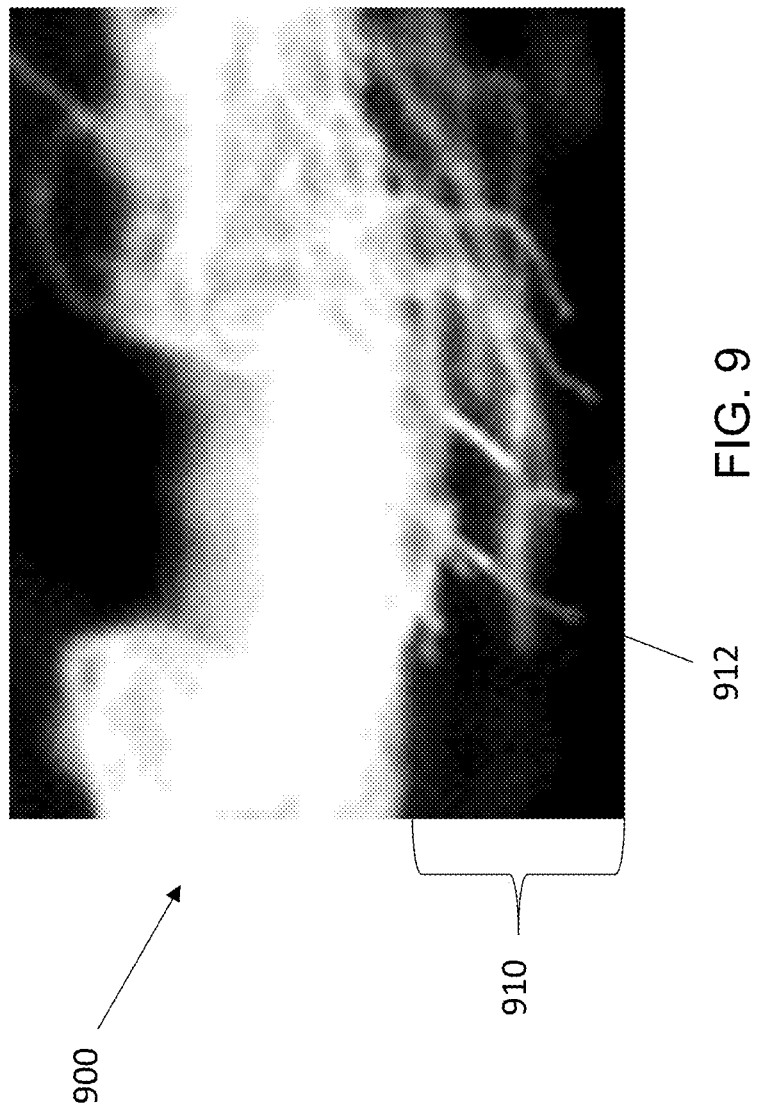
FIG. 9 is a photograph of a zoomed-in portion of the cross-section of the activated, lightweight, composite web of FIG. 8.

Referring now to FIG. 9 a selected area, which represents the multitudes of similar areas, is shown in a highly-magnified photograph 900. Photograph 900 shows a zone 910 with soft broken fiber ends 912 reoriented to nearly vertical. It is well known in the art of tactile sensation that thin, vertical fiber ends, such as those experienced in brushed cotton, for example, create a feeling of softness. U.S. Pat. No. 7,351,297, which is incorporated by reference, teaches an activation with a depth of engagement of the intermeshing gears that breaks apart some of the nonwoven's fibers, forming fiber ends which create a higher degree of softness. In this way, an activated nonwoven web with soft broken fiber ends reoriented to nearly vertical is concurrently formed. In the embodiment discussed herein, the nonwoven is a spun bond polypropylene web, or "SBPP" and has a basis weight, in grams per square meter, or gsm, of an average of 10 gsm.

The activated, lightweight, composite web 132 described above is not only lighter and softer than conventional webs of this type but it also has faster strikethrough time for synthetic urine. Strikethrough time testing is conducted using a Strikethrough Apparatus according to EDANA ERT 150.5-02 (including a funnel with magnetic valve, ring stand to support the funnel, strikethrough plate with electrodes, base plate, and electronic timer) sold under the name Lister by Lenzing Technik of Austria. The synthetic urine is a Saline Solution consisting of a 9 g/l solution of analytical grade sodium chloride in deionized water resulting in a surface tension of 70 mN/m (+/−2 mN/m) at 23° C. (+/−2° C.).

The web sample is cut to about 4 inches×4 inches and placed over a stack of absorbent papers. This stack is the placed under the Lister strikethrough plate and the plate's orifice is aligned with funnel's outlet. A sample of 10 ml of saline is introduced into the Lister plate orifice. When the saline is first present it touches electrical contacts in the orifice which creates an electrical circuit that starts a timer. Once the saline has struck through the web sample to be completely absorbed by the stack of papers, and thus has fully evacuated the plate's orifice, the circuit is broken which turns off the timer. In this way "Strikethrough Time" is determined and recorded. If strikethrough time is slower than a functional time, urine may accumulate on the surface and move laterally, leaking out of the diaper.

Many combinations of nonwovens and formed films have existed in the absorptive device market. Various uses are found such as acquisition layers and occasionally backsheets. They have not been generally used as topsheets, however, because they are heavy, lack softness, lack coolness and many have slower strikethrough times. It is desirable for the formed film of the composite web to have apertured protuberances with a mesh count of greater than 35 to yield an activated composite web that is lightweight and soft. In this embodiment, the mesh count was a 57 mesh and the composite web was vacuum form laminated at 11.7 gsm, which is a just under a half mil, which is considered to be very thin for a film. The apertures 314, 614, 616 are very small and not necessarily amenable for functional strikethrough time.

When un-activated webs, or webs of less than about 0.16 inches of activation depth, were tested for strikethrough time, they had high values that averaged around 2.85 seconds. With activation depths of 0.165 to about 0.180 inches, the strikethrough time dropped to 2.27 seconds, about 25% faster. Within the range of webs of the present invention, it is expected that they will have strikethrough times of less than or equal to about 2.5 seconds.

Absorptive devices where a layer of this web would be found highly functional, especially as a topsheet or as an enhancement layer below the topsheet, include but are not limited to, baby diapers, adult incontinence devices, feminine napkins including the inter-labial options, tampons, panty liners, mops, cleaning cloths, absorbent pads such as bed pads and spill pads, and the like. The web of the present invention is lightweight, soft and pliable and should perform well in any of these uses.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A method of manufacturing an activated composite web, comprising:
    laminating a film layer to a nonwoven web to form a composite web;
    forming a plurality of apertured protuberances in the film layer with a pin punching unit; and
    passing the composite web through intermeshing elements to form an activated composite web, the intermeshing elements being constructed and arranged to form a plurality of first lanes substantially unaffected by activation aligned in a first direction and having a first width in a second direction substantially perpendicular to the first direction, and a plurality of second lanes aligned in the first direction and having a second width less than the first width in the second direction in the activated composite web,
    wherein a first portion of the plurality of apertured protuberances forms a plurality of first apertured protuberances having a plurality of corresponding first apertures with first cross-sectional areas, the first apertured protuberances being located in the first lanes, and a second portion of the plurality of apertured protuberances forms a plurality of second apertured protuberances having a plurality of corresponding second apertures with second cross-sectional areas, each of the second cross-sectional areas being larger than each of the first cross-sectional areas, the second apertured protuberances being located in the second lanes, and
    wherein each of the first apertures has a first major axis substantially aligned in the first direction, and each of the second apertures has a second major axis substantially aligned in the second direction.

2. The method according to claim 1, wherein the film layer has a basis weight of between about 6 gsm and about 20 gsm.

3. The method according to claim 1, wherein the nonwoven web has a basis weight of between about 8 gsm and about 18 gsm.

4. The method according to claim 1, wherein the plurality of apertured protuberances are arranged in a pattern having a mesh count of at least 35.

5. An activated composite web, comprising a composite web having:
    a nonwoven layer; and
    a film layer attached to the nonwoven layer, the film layer comprising a plurality of apertured protuberances,
    wherein the composite web is activated by stretching with intermeshing elements to form the activated composite web comprising:
    a plurality of first lanes substantially unaffected by activation aligned in a first direction and having a first width in a second direction substantially perpendicular to the first direction, wherein a first portion of the plurality of apertured protuberances forms a plurality of first apertured protuberances having a plurality of corresponding first apertures with first cross-sectional areas, the first apertured protuberances located in the first lanes; and
    a plurality of second lanes aligned in the first direction and having a second width less than the first width in the second direction, the first lanes and the second lanes alternating with each other in the second direction, wherein a second portion of the plurality of apertured protuberances forms a plurality of second apertured protuberances having a plurality of corresponding second apertures with second cross-sectional areas, each of the second cross-sectional areas being larger than each of the first cross-sectional areas, the second apertured protuberances located in the second lanes,
    wherein each of the first apertures has a first major axis substantially aligned in the first direction, and each of the second apertures has a second major axis substantially aligned in the second direction.

6. The activated composite web according to claim 5, wherein the film layer has a basis weight of between about 6 gsm and about 20 gsm.

7. The activated composite web according to claim 5, wherein the nonwoven web has a basis weight of between about 8 gsm and about 18 gsm.

8. The activated composite web according to claim 5, wherein the plurality of apertured protuberances are arranged in a pattern having a mesh count of at least 35.

* * * * *